United States Patent [19]
Duffy et al.

[11] Patent Number: 5,800,387
[45] Date of Patent: Sep. 1, 1998

[54] SAFETY MONITORING APPARATUS FOR A PATIENT CARE SYSTEM

[75] Inventors: Robert J. Duffy, Poway; Lon M. Severe, San Diego, both of Calif.

[73] Assignee: Alaris Medical Systems, Inc., San Diego, Calif.

[21] Appl. No.: 726,882

[22] Filed: Oct. 4, 1996

[51] Int. Cl.⁶ .................................................. A61M 31/00
[52] U.S. Cl. .................................. 604/65; 604/66; 604/50
[58] Field of Search ............................... 604/65, 66, 67, 604/49, 50

[56] References Cited

U.S. PATENT DOCUMENTS

| | | | |
|---|---|---|---|
| 5,010,473 | 4/1991 | Jacobs | 604/65 |
| 5,304,127 | 4/1994 | Kawahara et al. | 604/65 |
| 5,356,378 | 10/1994 | Doan | 604/65 |
| 5,368,562 | 11/1994 | Blomquist et al. | 604/65 |

*Primary Examiner*—Michael Powell Buiz
*Assistant Examiner*—Daphna Shai
*Attorney, Agent, or Firm*—Pennie & Edmonds, LLP

[57] ABSTRACT

In accordance with the present invention, a safety monitoring apparatus provides protection in the event of an alarm condition or failure in a patient care system. More particularly, the safety monitoring apparatus is an independent functional unit within a device such as an infusion pump unit which provides single-fault protection in the event of an alarm condition or failure in the pump itself or in the primary control and monitoring means of the pump. The safety monitor utilizes control and signal inputs and can detect fault conditions independently of the primary control and monitoring means of the pump. Parameters which the safety monitoring apparatus may independently monitor in an infusion pump include motor control, air-in-line, flow-stop detection, mechanism motion, pressure sensing, door position sensing, and total volume infused. If a fault condition is sensed, the safety monitor can notify the primary control means, independently shut down fluid delivery, or sequentially do both.

25 Claims, 2 Drawing Sheets

SAFETY MONITORING APPARATUS FOR A PATIENT CARE SYSTEM

BACKGROUND OF THE INVENTION

Technical Field

The present invention relates to a safety monitoring apparatus for a patient care system. Specifically, the present invention relates to an apparatus for providing single-fault protection in the event of failure of the functional units of the patient care system or of the primary control and monitoring means of those functional units.

Discussion of the Related Art

Patent care systems, and in particular, patient care systems including infusion pumping units, are well known in the medical field. For example, U.S. Pat. No. 4,756,706 to Kerns et al. discloses a centrally managed infusion pump system in which pump and monitoring modules are attached to a central management unit. U.S. Pat. No. 4,898,578 to Rubalcaba, Jr. also discloses an infusion pump system which includes a plurality of infusion pump modules selectively attached to a central management unit.

U.S. Pat. No. 5,256,157 to Samiotes et al. discloses a programmable infusion pump for dispensing drugs in accordance with the requirements of a particular user. Specifically, the pump includes a microprocessor which communicates with a replaceable memory module so as to configure the pump to meet individual user needs. U.S. Pat. No. 5,100,380 to Epstein et al. also discloses an infusion system for administering multiple infusates at individually programmable rates, volumes, and sequences.

Related art patient care systems, which are generally designed to provide precise control of their functional units, also include various sensors to detect abnormalities during operation. For example, in the case of an infusion pump unit, alarm and fault conditions may be detected in various pump operation parameters, such as motor control, air-in-line, flow-stop detection, mechanism motion, pressure sensing, door position sensing, and total volume to be infused versus the preset volume to be infused. Related art systems can further include means to trigger audible and visual alarms and halt functionality should an alarm or fault condition occur.

However, related art systems in the medical field contain the disadvantage of being susceptible to failures of the primary control and monitoring means of their functional units. Thus, there exists a need in the art for a patient care system with an independent safety monitoring apparatus which provides protection in the event of failure of either the primary control and monitoring means of the functional units or of the functional units themselves.

OBJECTIVES AND SUMMARY OF THE INVENTION

In view of the above related art, it is an object of the present invention to provide increased fault tolerance through the use of a safety monitoring means that is independent of the primary control and monitoring means.

It is a further object of the invention to provide a safety monitoring means which can be fully encapsulated for increased system safety and cost effectiveness.

In accordance with the invention, a safety monitor provides protection in the event of an alarm or failure in a patient care system. The safety monitor is preferably an independent and encapsulized module within a functional unit, such as an infusion pumping unit, which provides single-fault protection in the event of failure of either the functional unit or the primary control and monitoring means of the functional unit. The safety monitor includes its own processing means, its own memory, and its own clock. The safety monitor utilizes control and signal inputs and can detect alarm and fault conditions independently of the primary control and monitoring means of the device. Parameters which the safety monitor may independently monitor in a functional unit such as an infusion pump include motor control, air-in-line, flow-stop detection, mechanism motion, pressure sensing, door position sensing, and total volume infused. If an alarm or fault condition is sensed, the safety monitor can notify the primary control means of the unit, independently shut down operation of the unit, or sequentially do both.

In an alternative embodiment of the invention, a patient care system is provided which includes a functional unit for providing patient therapies or for monitoring the condition of a patient, and a control system for controlling the functional unit.

The control system includes a means for sensing conditions indicative of the performance of the functional unit, and for providing signals in accordance with the sensed conditions. The control system also includes a primary control unit which includes a means for controlling the functional unit in accordance with certain predetermined information, a means for monitoring the functional unit by receiving signals from the sensor, and a means for providing information to a user regarding therapies provided or conditions monitored by the functional unit.

The control system further includes a safety monitoring unit, which includes a means for receiving signals from the sensor and the primary control unit, a means for monitoring the primary control unit and the functional unit using the received signals, a means for detecting an alarm condition or failure in the primary control unit or in the functional unit using the received signals, and a means for notifying the primary control unit or disabling the functional unit should such an alarm condition or failure be detected.

BRIEF DESCRIPTION OF THE DRAWINGS

These and other methods, structures, features, aspects, and advantages of the present invention will become more readily apparent from the following detailed description, which should be read in conjunction with the accompanying drawings, in which.

DETAILED DESCRIPTION OF THE INVENTION

Figure 1:
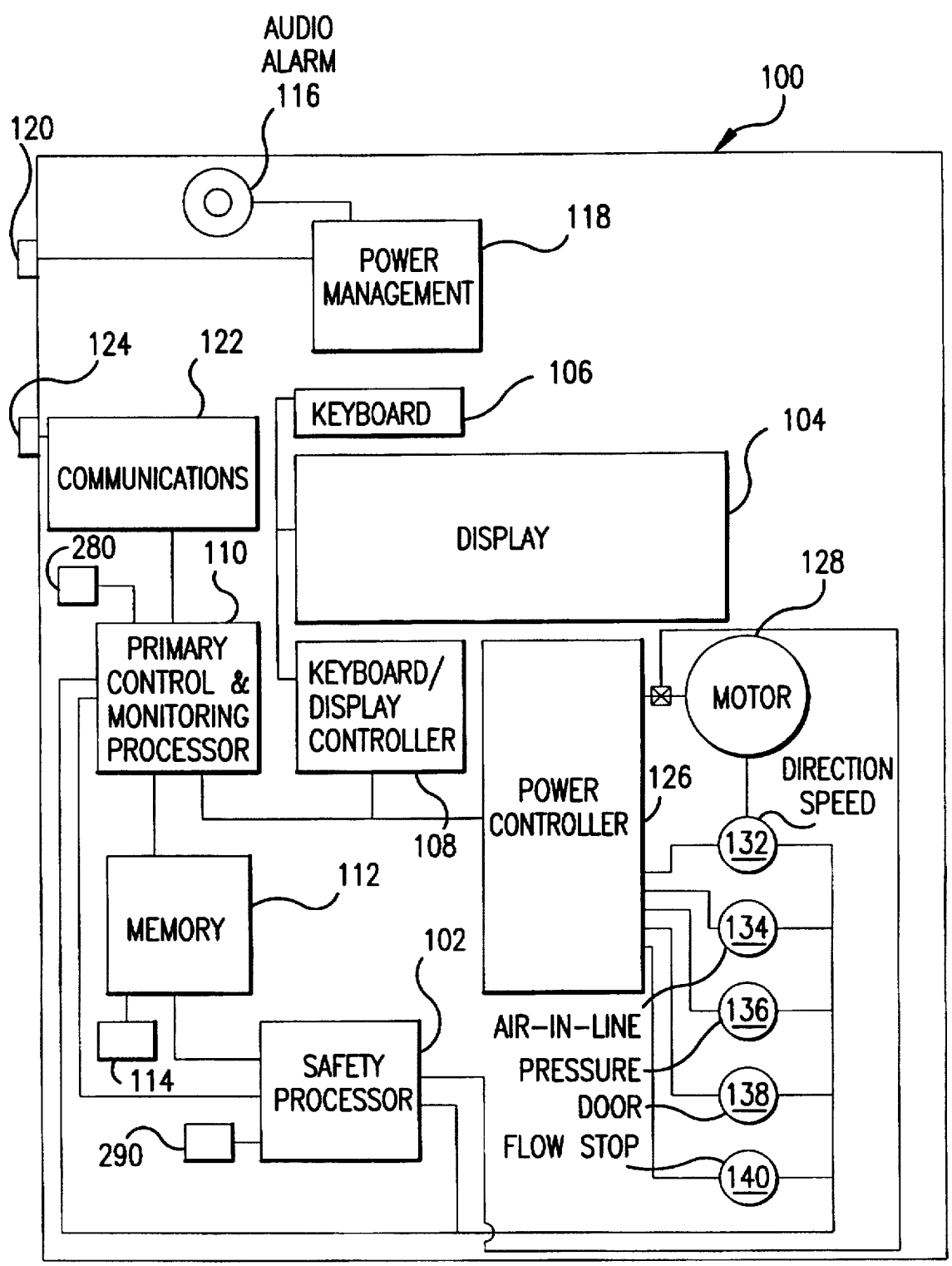
FIG. 1 discloses a block diagram of an infusion pumping unit including a safety monitoring apparatus.

The following embodiments of the present invention will be described in the context of a patient care system, although those skilled in the art will recognize that the disclosed methods and structures are readily adaptable for broader application. Note that whenever the same reference numeral is repeated with respect to different figures, it refers to the corresponding structure in each such figure.

FIG. 1 is a block diagram which discloses the various aspects of a control and monitoring system for an infusion pump unit 100 including a safety monitoring apparatus.

Although this exemplary and illustrative system is described below using an infusion pump unit, one skilled in the art will understand that the novel safety monitoring apparatus described herein could be applied to a variety of other different functional units and still fall within the scope of the present invention. As described in U.S. patent application Ser. No. 08/403,503, entitled MODULAR PATIENT CARE SYSTEM, and filed on Mar. 13, 1995 by the assignee of the present application, other possible functional units include a patient controlled analgesia (PCA) pump, syringe pump, pulse oximeter, electrocardiograph, and a blood pressure monitor. This application is incorporated herein in its entirety by reference.

In accordance with the present invention, infusion pump unit 100 may include well known infusion pump components such as a display 104, keyboard 106, and a keyboard/display controller 108. The system may also include a primary control and monitoring processor 110, associated memory 112, and clock 280 which allow infusion pump unit 100 to receive and process data and commands from both users and other patient care system components, such as blood pressure monitors and pulse oximeters. Primary control and monitoring processor 110 allows infusion pump unit 100 to perform various calculations including those required for a designated infusion utilizing data entered by the user. Memory 112 may include a battery backup 114 so as to maintain the information stored in memory when the pump unit is not receiving power from an external source. Battery backup 114 may also be used to power audio alarm 116, which may emit a signal illustratively when an infusion is complete or there is a failure of the main power source. Power manager 118 obtains power from power port 120 which may be connected to and receive power from other infusion pump units or other patient care system components. Power manager 118 distributes the power to the required components of infusion pump unit 100. Infusion pump unit 100 may also include an internal communications controller 122, which may send or accept data or commands from other patient care system components through communication port 124.

Infusion pump unit 100 also contains a power controller 126 and a pump motor 128. Power controller 126 and pump motor 128 may be comprised of any suitable pump motor/motor controller combination. Pump motor 128 acts to force fluid from a fluid reservoir through an infusion set to a vascular access device illustratively by peristaltic motion such as that disclosed in U.S. Pat. No. 5,165,873 to Meijer. It is to be further understood that one skilled in the art could choose from a variety of commercially available fluid reservoirs, sets, vascular access devices and other infusion materials to use in conjunction with infusion pump unit 100.

Infusion pump unit 100 also preferably includes a variety of sensors for detecting various operational parameters associated with a pumping unit. These sensors, the functionality, control, and monitoring of which is described in detail below, may include mechanism motion sensor 132, air-in-line sensor 134, fluid pressure sensor 136, door position sensor 138, and flow stop sensor 140.

Primary control and monitoring processor 110 receives and processes signals from these sensors which indicate the performance of a particular infusion. If primary processor 110 determines that an undesired event is occurring, the processor is capable of taking further action such as placing pump unit 100 in an advisory or alarm state, stopping the infusion, shutting down the pump unit, and/or forwarding information to other attached units via a central interface unit within the patient care system for full system shutdown.

Figure 2:
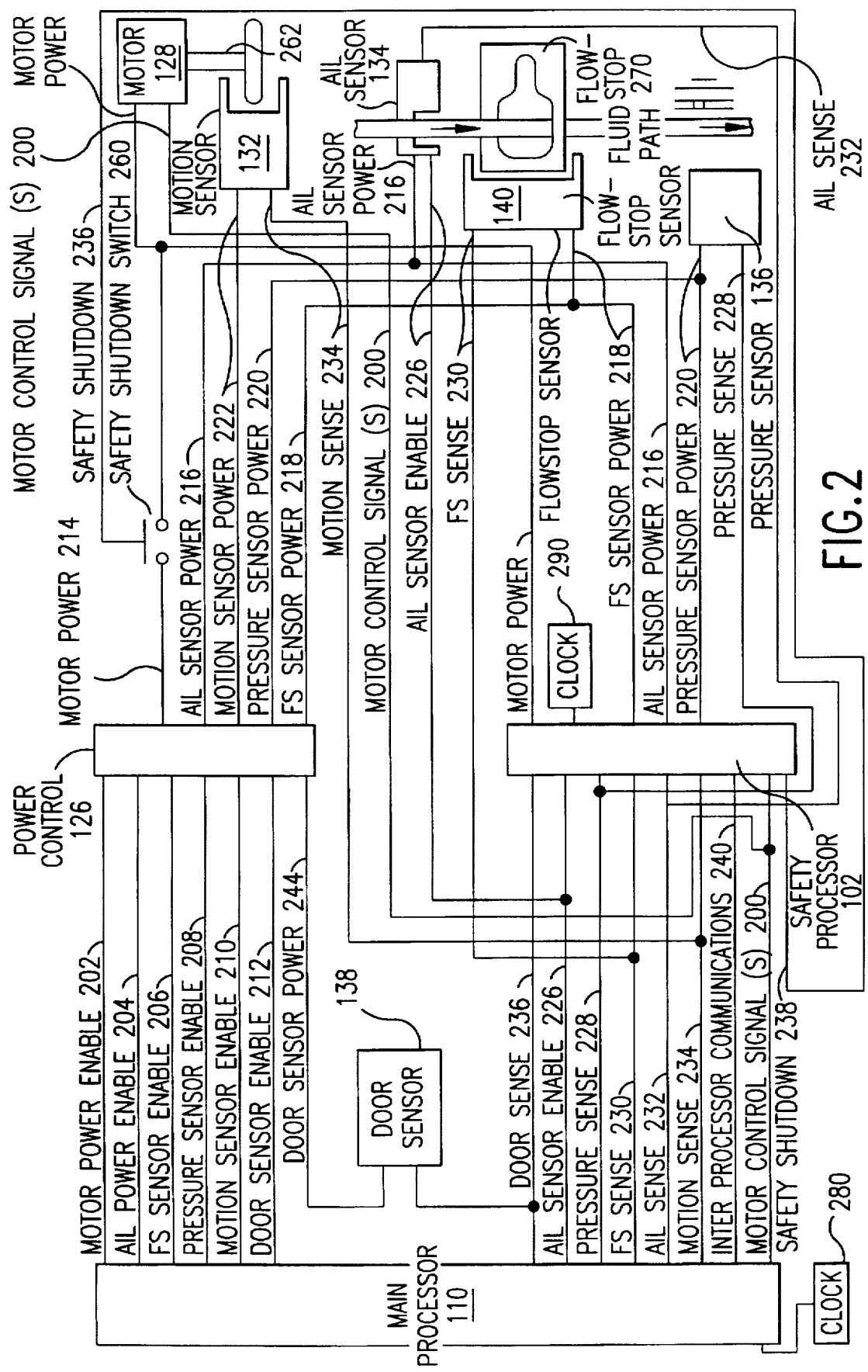
FIG. 2 discloses a detailed block diagram of an infusion pumping unit including a safety monitoring apparatus, including illustrative monitoring and control lines according to the invention.

In accordance with the present invention, infusion pump unit 100 additionally includes a safety processor 102 and safety processor clock 290 for providing single-fault protection in the event of failure of primary processor 110 or other system components. FIG. 2 discloses a detailed block diagram of the circuitry surrounding safety processor 102 and safety processor clock 290. Safety processor 102 may illustratively be implemented as a printed circuit board with discrete electronic components, or may be implemented using an application specific integrated circuit (ASIC).

Safety processor 102 may monitor the same signals from the sensors listed above which are also monitored by primary processor 110. As shown in FIG. 2, safety processor 102 may also receive additional pump operating parameters and information from primary processor 110 through the interprocessor communication line 240 so as to further ensure proper pump operation. Using these signals, and as described in detail below, safety processor 102 may independently monitor parameters relating to the infusion pump unit 100 such as motor control, mechanism motion, air-in-line, pressure sensing, door position sensing, flow-stop detection, and total volume to be infused versus the preset volume to be infused. If safety processor 102 determines that an undesired event is occurring with respect to any of these parameters, this information is forwarded to primary processor 110 for further action, or the safety processor may independently shut down the functional unit. What follows is a detailed description of the pump unit 100 and safety processor 102 operation as it relates to the above-listed pump parameters.

Motor Control

Proper motor operation and control is vital during patient infusions. Therefore, in accordance with a preferred embodiment of the invention, primary control and monitoring processor 110 establishes, based upon user input, the appropriate current fluid delivery rate for the pumping unit, also known as the "set rate". Primary processor 110 then generates control signals to pump motor 128 which control the pumping rate, and thus the fluid delivery rate, so as to be in accordance with the pre-established set rate. These control signals typically consist of a motor control signal 200, for controlling motor rate, and a motor power enable signal 202 for prompting power controller 126 to provide the appropriate power to motor 128 through motor power signal 214. Motor power signal 214 is passed through a safety shutdown switch 260, which is controlled by safety processor 102 using the safety shutdown control signal 238.

One illustrative example of this functionality is the case of a stepper motor, where motor power signal 214 is typically a constant voltage while motor control signal 200 is a series of step pulses, the phasing of which determines the direction and speed of the motor and thus the fluid flow rate.

Prior to operation, primary processor 110 also communicates the established set rate to safety processor 102 by means of inter-processor communication link 240. While infusion pump unit 100 is operating, safety processor 102 monitors motor power signal 214 and motor control signal 200 and determines if the signals are appropriate in the context of the current fluid delivery rate, or set rate, which has been obtained from primary processor 110. Thus, for example, if the set rate is zero, the motor signals should be appropriate for the "stopped" condition (i.e., there should be an absence of motor power and motor control signals). Likewise, if the set rate is a value other than zero, the safety processor 102 monitors the motor power and motor control signals, and using independent calculations, determines if they are within the bounds for proper motor operation.

As an illustrative example, if the infusion pump set rate is 50 ml/hr, and the particular motor step frequency is defined by the following equation:

$$f_{(ms)}(\text{cycles/sec}) = \frac{\text{Set Rate(ml/hr)}}{.0050(\text{ml/cycle})} \times \frac{1(\text{hr})}{3600(\text{sec})}$$

and, the period of time between cycles or motor steps is defined by the following equation:

$$T_{(ms)}(\text{sec/cycle}) = \frac{.0050(\text{ml/cycle})}{\text{Set Rate(ml/hr)}} \times \frac{3600(\text{sec})}{1(\text{hr})}$$

then, primary processor 110 will generate and provide motor steps to motor 128 at a frequency of $f_{(ms)}$ using motor control signal 200. In this example, safety processor 102 will measure the time period between motor steps as seen by the motor control signal 200, and will expect the time period to be $T_{(ms)}$ as determined by the above equation.

If it is determined that the motor is not functioning properly, safety processor 102 can either notify primary processor 110 using inter-processor communication link 240, stop fluid delivery by removing power to the motor using the safety shutdown signal 238 to safety shutdown switch 260, or sequentially do both.

Mechanism Motion

Infusion pump unit 100 may also utilize a second means to detect actual motion of the fluid delivery mechanism, since the monitoring of motor power and control signals alone, and as described above, does not guarantee fluid delivery. In particular, physical failures such as motor 128 failure or breakage of mechanical components connecting motor 128 to the physical components which effect fluid delivery (such as pumping fingers) may result in fault conditions in infusion pump unit 100 which would not be detected by monitoring motor power signal 214 and motor control signal 200 alone.

Therefore, primary processor 110 advantageously monitors signals from a separate motion sensor 132 which detects actual motion of the fluid delivery mechanism 262. Motion sensor 132 is energized with a motion sensor enable signal 210 from primary processor 110 which in turn prompts power control 126 to provide motion sensor power through motion sensor power line 222. Motion sensor 132 then produces a motion sense signal 234 which indicates motion of the fluid delivery mechanism.

Motion sense signal 234 may illustratively alternate between two states when there is physical motion of the fluid delivery mechanism. In this alternating-state embodiment, the frequency of motion sense signal 234 corresponds to the speed of the actual fluid delivery mechanism 262. If the frequency of the signal is not within the bounds expected for the current set rate, primary processor 110 can halt fluid delivery by removing power to motor 128 using motor power enable signal 202, motor control signals 200, or both.

In accordance with the invention, safety processor 102 independently monitors motion sensor 132 by using motion sensor enable signal 210 and motion sense signal 234 in the context of the current set rate obtained from primary processor 110 and the clock rate obtained from clock 290. Using these signals, and using independent calculations, safety processor 102 can determine if actual pumping mechanism operation is within the bounds of the current set rate. More particularly, safety processor can measure the frequency of the motion sense signal 234 using clock 290, and will expect that frequency to correspond to the frequency which corresponds to the current set rate. Safety processor 102 may calculate the frequency corresponding to the current set rate in the same manner as main processor 110.

If safety processor 102 detects a fault condition with respect to the mechanism motion, it can either notify primary processor 110 using communication link 240, independently shut down the fluid delivery by removing power to motor 128 using safety switch 260, or sequentially do both.

Using the independent time base (clock 290) of safety processor 102 to determine the frequency of the motion sense signal 234 will also result in the detection of a failure or malfunction of primary processor clock 280. This is advantageous as clock failures are in many instances difficult to detect, especially in the situation where clock 280 continues to generate a clock signal but at an improper frequency. However, by utilizing clock signals from clock 290 to calculate the actual motor frequency, any malfunction of the primary clock 280 will be detected by safety processor 102 and will result in a fault condition.

Indeed, it will be understood by one skilled in the art that the use of the independent time base (clock 290) of safety processor 102 in monitoring any infusion pump operating parameters described herein, and in particular, motor control, air-in-line, and total volume infused versus the preset volume to be infused, will result in the detection by safety processor 102 of a failure or malfunction of primary processor clock 280.

Air-In-Line

The infusion of air to a patient's circulatory system can be hazardous in a number of clinical situations. Factors which relate to the level of danger to a particular patient during a particular infusion include the amount of air delivered during the infusion, the time period over which the amount of air is delivered, the size and circulatory fluid volume of the patient, and the physical condition of the patient.

Those skilled in the art will understand that commercially available infusion pump systems which are designed to provide precise control of the rate of fluid infusion will generally include a means for detecting air in the fluid delivery path, that is, air-in-line (AIL) detection. These systems will typically include additional means to trigger audible and visual alarms and stop fluid delivery should an alarm condition occur.

Two types of air-in-line situations can result in an alarm condition within infusion pump unit 100. A single air bolus may exceed a predetermined volume or accumulated air may exceed a predetermined volume within a particular time period.

In accordance with the invention, infusion pump unit 100 includes a method for determining whether a single air bolus exceeds a predetermined volume or whether the accumulated air within a particular time period exceeds a predetermined volume. The latter capability provides an added level of safety by detecting the delivery of a series of air bubbles which do not exceed the single bolus threshold, but whose accumulated air total may be a hazard in certain clinical situations.

Specifically, primary processor 110 generates or controls signals to an air-in-line sensor 134 which can detect the presence of air within the fluid delivery path. These signals typically consist of AIL sensor power 204, AIL sensor enable 226, AIL sense 232, a clock or other timebase, and either motion sense signal 234 or motor control signals 200. AIL sensor 134 is enabled using AIL sensor enable signal 226. Once enabled, the AIL sense signal 232 will assume one of two states based on whether the AIL sensor detects air or fluid in the line at that particular moment. When air is detected, a clock or other timebase and either motion sense 234 or motor control signals 200 are then used by processor 110 to measure the amount of air detected. If the amount of air detected exceeds a predetermined limit, an AIL alarm will be triggered.

More specifically, primary processor 110 first establishes the appropriate single bolus AIL limit and the appropriate accumulated air limit for pumping unit 100 and communicates them to safety processor 102 by means of the interprocessor communication link 240. At appropriate intervals which may be prescribed by the set rate, primary processor 110 provides power to the AIL sensor 134 using the AIL power enable signal 204 and Power Control 126, which generates AIL sensor power 216. Primary processor 110 enables the AIL Sensor 136 using the AIL sensor enable signal 226 and monitors the AIL sense signal 232 from the AIL sensor so as to determine if the sensor detects air or fluid. If sensor 136 detects air, primary processor starts a timer based on its own clock or timebase at an initial time T1. At a later time T2, processor 110 powers up and enables the AIL sensor 136 once again, monitors the AIL sense signal from the AIL sensor, and determines if the sensor detects air or fluid. If sensor 136 still detects air at time T2, primary processor 110 uses the motion sense signal (which indicates the actual delivery rate) and the timebase (indicating the actual time between T1 and T2) to determine the volume of air delivered between T1 and T2. This volume can be added to a single air bolus total and to an accumulated air total. The single air bolus total is then compared to the single bolus AIL limit, the accumulated air total is compared to the accumulated air limit, and if either limit is exceeded, primary processor 110 can stop the fluid delivery by removing power to motor 128 using the motor power enable signal 202 and/or motor control signals 200, and may also trigger an AIL alarm.

Advantageously, safety processor 102 monitors the motion sense signal 234, AIL sensor power signal 216, and AIL sense signal 232, and using independent clock 290 and independent calculations, also keeps track of the single air bolus total and accumulated air total in the manner described above. The single air bolus total may then be compared to the single bolus AIL limit, and the accumulated air total may then be compared to the accumulated AIL limit, and if either are exceeded, safety processor 102 can notify primary processor 110 using communication link 240, stop the fluid delivery by removing power to motor 128 using safety switch 260, or sequentially do both.

This novel method of AIL detection will now be more specifically described in the context of determining whether an accumulated AIL maximum of 1 ml over a 15 minute period has been exceeded, or whether a single bolus AIL limit of 75 ul has been exceeded. However, it will be apparent to one skilled in the art that this method could be used for other thresholds and other time periods.

In a preferred embodiment, a ring buffer with one minute intervals may be used to determine the amount of air accumulation. A ring buffer consists of a set of elements which correspond to the accumulated air within a fixed time interval. The number of elements in the ring buffer is determined by the predetermined accumulated AIL period, which in this particular example could be fifteen 1-minute intervals for a total 15 minute accumulated AIL period. The ring buffer may also advantageously include an additional element (in this case a sixteenth element). With this additional element, a 16 element ring buffer representing a 16 minute accumulation period may then be checked against a maximum limit for a 15 minute accumulation period, creating a one minute margin of error and thus an increased margin of safety.

The ring buffer may include a bin-pointer which designates the element (or bin) of the ring for the current 1-minute time interval. When the 1-minute time interval is complete, the bin-pointer is moved to the next element of the ring buffer. Thus, at any given moment, the bin-pointer points to the current 1-minute interval, the previous bin corresponds to the previous 1-minute interval, and the next bin corresponds to the 1-minute time interval 15 minutes prior to the current interval. Using this method, the accumulated AIL for each 1-minute period over the last 15 minutes is contained in the elements (or bins) of the ring buffer, and the sum of all elements is the total accumulated air for the past 15 minutes.

More particularly, and as mentioned previously, if sensor 136 still detects air at time T2, primary processor 110 determines the volume of air delivered between T1 and T2. This volume can be added to a single air bolus total and to the accumulated air total for the current 1 minute interval. The single air bolus total is then compared to the single bolus AIL limit of 75 ul, the accumulated air total for the 15 minute period is compared to the accumulated air limit of 1 ml, and if either limit is exceeded, primary processor 110 can stop the fluid delivery by removing power to motor 128 using the motor power enable signal 202 and/or motor control signals 200, and may also trigger an AIL alarm.

Pressure Sensing

Infusion pump unit 100 may also utilize one or more pressure sensors 136 to determine occlusion of the fluid delivery path and a resultant lack of fluid movement. In accordance with the invention, primary processor 110 generates or controls signals to a pressure sensor 136 which detects whether an intravenous (IV) tube is attached to the pump, and if so, detects the fluid pressure within the IV tube. The signals generated and controlled by primary processor 110 may illustratively consist of pressure sensor enable 208 and pressure sense 228. Pressure sensor 136 may be enabled by processor 110 at appropriate intervals through the pressure sensor enable signal 208, which prompts power control 126 to provide power to the sensor through pressure sensor power line 220. Once pressure sensor 136 has been enabled, sensor 136 will generate a pressure sense signal 228 indicating the pressure of the IV tube against the sensor. The pressure against the sensor can be correlated to the fluid pressure within the fluid path (IV tube) by primary processor 110. If the correlated fluid pressure falls outside a predetermined limit, an audible and visual occlusion alarm can be triggered and processor 110 can halt fluid delivery by removing power to motor 128 using motor power enable 202 or motor control signals 200.

Occlusion alarms can be either fluid source (bottle) side, patient side, or both. More specifically, in the instance of a fluid source side occlusion, the tubing between the fluid source and the infusion pump is occluded. The pumping action of the infusion pump will create a vacuum in the fluid path, which in turn will be sensed by a first pressure sensor 136. When this pressure falls below a predetermined limit, a fluid source side occlusion alarm condition is generated.

In the instance of a patient side occlusion, the tubing between the infusion pump and the patient's vascular access is occluded. The pumping action of the infusion pump will create increasing pressure in the fluid path, which will be sensed by a second pressure sensor 136. When this pressure exceeds a predetermined limit, a patient side occlusion alarm condition is generated.

Safety processor 102 beneficially monitors pressure sensors 136 independently of primary processor 110, and uses pressure sensor power signal 220 and pressure sense signal 228 in the context of the predetermined pressure limit, and determines if there is an occlusion of the fluid path in the same manner as primary processor 110. The predetermined pressure limit may be obtained from primary processor 110 through communication link 240. If safety processor 102 detects an occlusion, it can either notify the primary processor 110, independently shut down the fluid delivery using safety switch 260, or sequentially do both.

Door Position Sensing

Infusion pump unit 100 may include a mechanical door to capture the IV tube for control of fluid delivery and to prevent unintended free flow of fluid while the IV tube is attached to the pump. Accordingly, primary processor 110 generates or controls signals to a door sensor 138 which can detect the presence and state of the door within pump unit 100. The signals generated or controlled by primary processor 110 may consist of door sensor enable 212 and door sense 236. Door sensor 138 is enabled with the door sensor enable signal 212, which prompts power control 126 to provide power through door sensor power signal 244 to door sensor 138. Once door sensor 138 is enabled, door sense signal 236 can illustratively assume one of two states based upon whether the door is in an "open" or "closed" state.

More specifically, primary processor establishes an appropriate fluid delivery rate or set rate. Although, as explained above, the set rate can assume a wide range of values, the fluid delivery state of the pumping unit may be described as either "infusing" (set rate>0) or "stopped" (set rate=0). Thus, primary processor 110 can monitor the door sense signal 236 from door sensor 138 and determine if the state of the door is acceptable for the current set rate. If the pump is "infusing" (set rate>0), door sensor 138 should indicate a "door closed" condition. Alternatively, if the pump is "stopped" (set rate=0), it is acceptable for the door sensor 138 to indicate a "door open" condition. If an unacceptable condition is sensed, primary processor 110 can stop fluid delivery by removing power to the motor using the motor power enable signal 202 and/or motor control signal(s) 200, and trigger an alarm.

Safety processor 102 monitors door sensor 138 independently of the primary processor means, and uses door sensor power signal 224, door sense enable 212 and door sense 236 in context of the current fluid delivery rate (the set rate) to determine if the door state is appropriate for the current fluid delivery rate. If safety processor 102 detects an alarm or fault condition, it can either notify the primary processor 110, independently shut down the fluid delivery using safety switch 260, or sequentially do both.

Flow-Stop Detection

Infusion pump unit 100 may utilize a flow-stop device 270 independently of well known roller or slide clamps to prevent unintended free flow of fluid. Accordingly, primary processor 110 generates or controls signals to a flow-stop sensor 140 which detects both the presence of the flow-stop device 270 within the pump and the state of the flow-stop device 270 with respect to the fluid delivery path. These signals may include a flow-stop sensor enable signal 206 and a flow-stop sense signal 230.

Flow-stop sensor 140 may be powered using flow-stop sensor enable signal 206 from processor 110, which prompts power control 126 to provide power to the sensor through flow-stop sensor power line 218. Once enabled, flow-stop sense signal 230 from the sensor may illustratively assume one of two states based on whether the flow-stop device 270 is in the pump and in either an "occluded" or "unoccluded" state.

Specifically, primary processor 110 establishes the appropriate current fluid delivery rate, or set rate, for the infusion pump unit 110. Primary processor 110 communicates this set rate to safety processor 102 by means of communication link 240. At appropriate intervals which may be prescribed by the set rate, processor 110 enables power to flow-stop sensor 140 using flow-stop sensor enable signal 206 and power control 126, which generates flow-stop sensor power 218. Primary processor 110 monitors flow-stop sense signal 230 from flow-stop sensor 140, as well as door sense signal 236 from door sensor 138, and determines if the combination of signals is appropriate for the current set rate.

More specifically, if pump unit 100 is "infusing" (set rate>0), door sense signal 236 should indicate a "door closed" condition and flow-stop sense signal 230 should indicate an "unoccluded" state for the flow-stop device 270. If an abnormality is detected, primary processor 110 can stop the fluid delivery by removing power to motor 128 using the motor power enable signal 202 or the motor control signals 200.

If the pump unit 100 is "stopped" (set rate=0) and the door sense signal indicates a "door closed" condition, the flow-stop sense signal 230 should indicate an "unoccluded" state for the flow-stop device 270. If the flow-stop sense signal 230 indicates the "occluded" state for the flow-stop device 270, this would indicate a failure of either the flow-stop device 270 or the flow-stop sensor 140. In this situation, primary processor 110 can trigger a fault alarm. Conversely, if pump unit 100 is "stopped" (set rate=0) and the door sense signal 230 indicates a "door open" condition, the flow-stop sense signal 230 should indicate an "occluded" state for the flow-stop to prevent free flow. If flow-stop sense signal 230 indicates the "unoccluded" state for the flow-stop device, primary processor 110 can trigger a "door open" or "free flow" alarm.

In accordance with the invention, safety processor 102 independently monitors the flow-stop sensor power signal 218, door sense signal 236, and flow-stop sense signal 230, and determines if they are appropriate for the current set rate in the same manner as primary processor 110. If they are not, safety processor 102 can notify primary processor 110 using the communication link 240, stop the fluid delivery by removing power to motor 128 using the safety switch 260, or sequentially do both.

Total Volume Infused Versus Volume To Be Infused (VTBI)

As previously discussed, primary processor 110 generates or controls signals to motor 128 which regulates fluid delivery rate and volume. These signals typically consist of motor power enable 202 and a second signal or set of signals 200 which control motor rate. As also mentioned, in the illustrative case of a stepper motor, the motor power signal 202 is typically a constant voltage required to operate the motor, while motor control signal 200 is a series of step pulses the phasing and pulse interval of which determines the direction and speed of the motor (which correlates to a particular fluid flow rate).

Over time, the flow rate can be used to determine the total volume infused. Typically, the user will preset a Volume To Be Infused (VTBI). Primary processor can communicate this preset VTBI to safety processor 102 through communication link 240. Primary processor can then utilize motion sense signal 234 and its clock 280 to keep track of the total volume being infused. Once the total volume infused reaches the preset VTBI, primary processor 102 should preferably either stop fluid delivery by infusion pump unit 100 or provide a minimal flow rate required to prevent blood coagulation and occlusion of the venous access. The flow rate can be minimized using motor control signals 200.

Safety processor 102 also monitors the motion sense signal 234, and using its own independent clock 290 and independent calculations, keeps track of the total volume infused. If the total volume infused exceeds the VTBI (which the safety processor 102 receives from the primary processor 110), safety processor 102 can notify the primary processor 110 using communication link 240, stop fluid delivery by removing power to motor 128 using safety switch 260, or sequentially do both.

More particularly, primary processor 100 starts with an initial VTBI, and decrements the VTBI periodically using the following equations:

*Set Rate×elapsed time=volume delivered*

*Initial VTBI−volume delivered=Remaining VTBI*

If the Remaining VTBI reaches zero, the infusion is completed. In accordance with the invention, safety processor 102 starts with an initial volume infused of zero and increments the total volume infused (TVI) using the following equation:

$$TVI(ml) = \frac{\text{elapsed time (sec)}}{T_{(ms)}(\text{sec/cyc})} \times .0050(\text{ml/cyc})$$

If the total volume infused (TVI) is greater than or equal to the Initial VTBI, then an alarm condition occurs and safety processor 102 can take any of the necessary steps described above.

Various embodiments of the invention have been described. The descriptions are intended to be illustrative, not limitative. Thus, it will be apparent to those skilled in the art that modifications may be made to the invention as described without departing from the scope of the claims set out below.

We claim:

1. A patient care system, comprising:
   a functional unit adapted to provide patient therapies or monitor the condition of a patient; and
   a control system for controlling said functional unit, said control system including:
   a sensor for sensing conditions indicative of the performance of said functional unit, said sensor including means for providing signals in accordance with said sensed conditions;
   a primary control unit, which: (1) controls said functional unit in accordance with predetermined information, (2) monitors said functional unit by receiving signals from said sensor, and (3) provides information to a user regarding therapies provided or conditions monitored by said functional unit; and
   a safety monitoring unit, which: (1) receives signals from said sensor and said primary control unit, (2) monitors said primary control unit and said functional unit using the received signals, (3) detects an alarm condition or failure in the primary control unit or in the functional unit using the received signals, and (4) notifies said primary control unit or disables said functional unit should such alarm condition or failure be detected.

2. The system according to claim 1, wherein said functional unit is an infusion system including a motor for administering fluids to a patient through a fluid delivery path.

3. The system according to claim 2, wherein said sensor is an air-in-line sensor for detecting the presence of air in the fluid delivery path.

4. The system according to claim 2, wherein said functional unit includes a flow-stop device for preventing unintended fluid flow and wherein said sensor is a flow-stop sensor for detecting the state of said flow-stop device.

5. The system according to claim 1, wherein said functional unit includes a door and said sensor is a door sensor for detecting the state of said door.

6. The system according to claim 1, wherein said primary control unit includes a first processing means and a first memory, and said safety monitoring unit includes a second processing means and a second memory.

7. The system according to claim 6, wherein said primary control unit includes a first timing device and said safety monitoring unit includes a second timing device.

8. The system according to claim 2, wherein said primary control unit controls said motor using motor control signals, and wherein said safety monitoring unit receives said motor control signals from said primary control unit and detects an alarm condition or failure in said primary control unit using said motor signals.

9. The system according to claim 1, wherein said safety monitoring unit, in order to detect an alarm condition or failure in the primary control unit or in the functional unit using the received signals:
   determines whether the received signals are in accordance with proper primary control unit and functional unit operation; and
   triggers an alarm should the received signals indicate an alarm condition or failure in the primary control unit or in the functional unit.

10. An infusion system for administering fluids to a patient through a fluid delivery path, comprising:
    means for infusing fluids into the patient;
    a sensor for sensing conditions indicative of the performance of said infusing means, said sensor including means for providing signals in accordance with said sensed conditions;
    a primary control unit including a first processing means, said unit adapted to control said infusion means in accordance with predetermined information, to monitor said infusion means by receiving signals from said sensor, and to provide information to a user regarding infusions; and
    a safety monitoring unit including a second processing means, said unit adapted to receive signals from said sensor and said primary control unit, to monitor said primary control unit and said infusion means using the received signals, to detect an alarm condition or failure in the primary control unit or in the infusion means, and to notify said primary control unit or disable said infusion means should such failures be detected.

11. The system according to claim 10, wherein said sensor is an air-in-line sensor for detecting the presence of air in the fluid delivery path.

12. The system according to claim 10, wherein said sensor is a pressure sensor for detecting an occlusion of the fluid delivery path.

13. The system according to claim 10, wherein said infusing means includes a motor and said sensor is a motion sensor for detecting movement of said motor.

14. The system according to claim 10, wherein said primary control unit further includes a first memory and a first clock, and said safety monitoring unit further includes a second memory and a second clock.

15. An infusion system for administering fluids to a patient through a fluid delivery path, comprising:

an infusion pump assembly including a motor and pumping element for infusing fluids into the patient;

an air-in-line sensor for detecting the presence of air in the fluid delivery path, said sensor including means for providing signals indicating when air is sensed in the fluid delivery path;

a primary control unit including a first processing means, a first memory, and a first clock, said unit adapted to control said infusion pump unit and said air-in-line sensor in accordance with information provided by a user, monitor said infusion pump unit by receiving signals from said air-in-line sensor indicating the presence of air in the fluid delivery path, provide information to a user regarding infusion pump unit operation, detect an alarm condition or failure in the infusion pump unit, and provide and alarm to the user or disable said infusion pump unit should such alarm condition or failure be detected; and a safety monitoring unit including a second processing means, a second memory, and a second clock, said unit adapted to receive signals from said air-in-line sensor indicating the presence of air and signals from said primary control unit indicating when said sensor is enabled, monitor said primary control unit and said infusion pump unit using the received signals, detect an alarm condition or failure in the primary control unit or in the infusion pump unit, and notify said primary control unit or disable said infusion pump unit should such alarm condition or failure be detected.

16. The infusion system of claim 15, further comprising a flow-stop device and a flow-stop sensor for detecting the state of said flow-stop device, said primary control unit and said safety monitoring unit each further adapted to receive signals from said flow-stop sensor for monitoring the operation of said infusion pump unit.

17. A patient care system, comprising:

a functional unit adapted to provide patient therapies or monitor the condition of a patient; and a control system for controlling said functional unit, said control system including:

a sensor for sensing conditions indicative of the performance of said functional unit, said sensor including means for providing signals in accordance with said sensed conditions;

a primary control unit, including: (1) means for controlling said functional unit in accordance with predetermined information, (2) means for monitoring said functional unit by receiving signals from said sensor, and (3) means for providing information to a user regarding therapies provided or conditions monitored by said functional unit; and a safety monitoring unit, including: (1) means for receiving signals from said sensor and said primary control unit, (2) means for monitoring said primary control unit and said functional unit using the received signals, (3) means for detecting an alarm condition or failure in the primary control unit or in the functional unit using the received signals, and (4) means for notifying said primary control unit or disabling said functional unit should such alarm condition or failure be detected.

18. The system according to claim 17, wherein said functional unit is an infusion system including a motor for administering fluids to a patient through a fluid delivery path.

19. The system according to claim 18, wherein said sensor is an air-in-line sensor for detecting the presence of air in the fluid delivery path.

20. The system according to claim 17, wherein said primary control unit includes a first processing means and a first memory, and said safety monitoring unit includes a second processing means and a second memory.

21. The system according to claim 20, wherein said primary control unit includes a first timing device and said safety monitoring unit includes a second timing device.

22. The system according to claim 17, wherein said safety monitoring unit detection means further includes:

means for determining whether the received signals are in accordance with proper primary control unit and functional unit operation; and means for triggering an alarm should the received signals indicate an alarm condition or failure in the primary control unit or in the functional unit.

23. A method for ensuring proper functioning of an infusion pump unit with a fluid delivery path, comprising the steps of:

infusing fluids into a patient through said fluid delivery path;

providing an air-in-line sensor for detecting the presence of air in the fluid delivery path;

enabling said air-in-line sensor with a primary control unit;

controlling the operation of said air-in-line sensor with said primary control unit;

detecting the presence of air in the fluid delivery path with said air-in-line sensor; indicating to said primary control unit with said air-in-line sensor that air is present in said fluid delivery path;

indicating to a safety monitoring unit with said air-in-line sensor that air is present in said fluid delivery path;

determining whether the detected air-in-line exceeds a predetermined maximum with both said primary control unit and said safety monitoring unit; and triggering an alarm with either said primary control unit or said safety monitoring unit should the detected air-in-line exceed the predetermined maximum.

24. The method of claim 23, further comprising the step of halting the infusion of fluids to the patient should the detected air-in-line exceed the predetermined maximum.

25. The method of claim 23, wherein said primary control unit includes a first processing means, a first memory, and a first clock, and said safety monitoring unit includes a second processing means, a second memory, and a second clock.

* * * * *